(12) United States Patent
Malik et al.

(10) Patent No.: US 6,998,040 B2
(45) Date of Patent: Feb. 14, 2006

(54) SOL-GEL OPEN TUBULAR ODS COLUMNS WITH CHARGED INNER SURFACE FOR CAPILLARY ELECTROCHROMATOGRAPHY

(75) Inventors: Abdul Malik, Tampa, FL (US); James D. Hayes, Tampa, FL (US)

(73) Assignee: University of South Florida, Tampa, FL (US)

( * ) Notice: Subject to any disclaimer, the term of this patent is extended or adjusted under 35 U.S.C. 154(b) by 188 days.

(21) Appl. No.: 10/057,080

(22) Filed: Jan. 24, 2002

(65) Prior Publication Data

US 2003/0075447 A1 Apr. 24, 2003

Related U.S. Application Data

(60) Provisional application No. 60/263,988, filed on Jan. 24, 2001.

(51) Int. Cl.
*B01D 15/08* (2006.01)

(52) U.S. Cl. ............... 210/198.2; 210/502.1; 210/635; 210/656; 204/600

(58) Field of Classification Search ............. 210/198.2, 210/635, 656, 659, 502.1; 436/161, 178; 422/70; 204/450, 600
See application file for complete search history.

(56) References Cited

U.S. PATENT DOCUMENTS

| | | | | |
|---|---|---|---|---|
| 4,123,931 A | * | 11/1978 | Blaser | 73/23.39 |
| 5,145,579 A | * | 9/1992 | Eguchi et al. | 210/198.2 |
| 5,431,807 A | * | 7/1995 | Frechet et al. | 210/198.2 |
| 5,624,875 A | * | 4/1997 | Nakanishi et al. | 501/39 |
| 6,136,187 A | * | 10/2000 | Zare et al. | 210/198.2 |
| 6,210,570 B1 | * | 4/2001 | Holloway | 210/198.2 |
| 6,562,744 B1 | * | 5/2003 | Nakanishi et al. | 501/39 |
| 2003/0213732 A1 | * | 11/2003 | Malik et al. | 210/94 |

OTHER PUBLICATIONS

Snyder, (Introduction to Modern Liquid Chromatography, John Wiley & Sons, New York (1979), pp. 278-280.*
Bigham, S., et al., "Sol-Gel Capillary Microextraction," Anal. Chem. vol. 74, No. 4, pp. 752-761, 2002.
Bruin, G. et al., "Electrically driven open-tubular liquid chromatography," Journal of Chromatography, 517, pp. 557-572, 1990.

(Continued)

*Primary Examiner*—Ernest G. Therkorn
(74) *Attorney, Agent, or Firm*—Saliwanchik, Lloyd & Saliwanchik

(57) ABSTRACT

The present invention provides for a column for use in capillary electrochromatography including a tube, wherein the tube includes an inner surface having a positively or negatively charged, chemically-bonded stationary coating thereon. The present invention further provides for a method of making a column for use in capillary electrochromatography, including a tube, wherein the tube includes an inner surface having a positively or negatively charged chemically-bonded stationary coating thereon, wherein the steps include filling the column with a sol-gel solution, maintaining the sol-gel solution within the column, and forcing the sol-gel solution out of the column with an inert gas. Further, the present invention provides for a method of analytical separation with a column including an inner layer having a positively charged chemically-bonded stationary coating thereon that reverses the direction of electroosmotic flow in the column compared with a column without the positive surface charge. Additionally, the present invention provides for a method of using a column including an inner layer of positively charged chemically-bonded stationary coating thereon by introducing a sample into the column operating under reversed electroosmotic flow due to positively charged chemically-bonded stationary coating.

16 Claims, 9 Drawing Sheets

OTHER PUBLICATIONS

Chong, S. et al., "Sol-Gel Coating Technology for the Preparation of Solid-Phase Microextraction Fibers of Enhanced Thermal Stability," Anal. Chem., 69, pp. 3339-3898, 1997.

Dittmann, M. et al., "Capillary Electrochromatography: Investigation of the Influence of Mobile Phase and Stationary Phase Properties on Electroosmotic Velocity, Retention, and Selectivity," J. Microcolumn., 9, pp. 399-408, John Wiley & Sons, Inc. 1997.

Folestad, S. et al., "Performance and preparation of immobilized polysiloxane stationary phases in 5-55 µm I.D. open-tubular fused silica columns for liquid chromatography," Abstract, Journal of Chromatography, vol. 391, pp. 347-372, 1987. (Abstract only).

Garner, T.W. et al., "Increased selectivity for electrochromatography by dynamic ion exchange," Abstract, Journal of Chromatography, vol. 640, pp. 397-402, 1993. (Abstract only).

Göhlin, K. et al., "Study of polyorganosiloxanes (native and solvent swollen) for the preparation of narrow (5-15 µm I.D.) and long (1-6m) open tubular columns in reversed-phase liquid chromatography," Abstract, Journal of Chromatography, vol. 645, pp. 41-56, 1993. (Abstract only).

Göhlin, K. et al., "Narrow (5-50 µm I.D.) Open Tubular Columns in Liquid Chromatography Using Immobilizing Polymethyl-octadecylsiloxane as Stationary Phase," Journal of Microcolumn, Sep. 3, pp. 547-556, 1991.

Guo, Y., et al., "A Stationary Phase for Open Tubular Liquid Chromatography and Electrochromatography Using Sol-Gel Technology," Anal. Chem., 67, pp. 2511-2516, 1995.

Hayes, J. et al., "Sol-gel chemistry-based Ucon-coated columns for capillary electrophoresis," Journal of Chromatography, vol. 695, pp. 3-13, 1997.

Hayes, J.D. et al., "Sol-Gel Monolithic Columns with Reversed Electroosmotic Flow for Capillary Electrochromatography," Anal. Chem., 72, pp. 4090-4099, 2000.

Hibi, K. et al., "Studies of open-tubular microcapillary liquid chromatography, III. β, β'- oxydipropionitrile and ethylene glycol stationary phases," Abstract, Journal of Chromatography, vol. 175, pp. 105-111, 1979. Abstract Only.

Ishli, D. et al., "Studies of open-tubular microcapillary liquid chromatography, IV. Soda-lime glass columns treated with alkaline solution," Abstract, Journal of Chromatography, vol. 185, pp. 73-78, 1979. Abstract Only.

Jorgenson, J. et al., "New techniques for liquid chromatography in open-tubular columns," Abstract, Journal of Pharmaceutical and Biomedical Analysis, vol. 2, pp. 191-196, 1984. Abstract Only.

Jorgenson, J.W. et al., "Liquid chromatography in open-tubular columns—Theory of column optimization with limited pressure and analysis time, and fabrication of chemically bonded reversed-phase columns on etched borosilicate glass capillaries," Abstract, Journal of Chromatography, vol. 255, pp. 335-348, 1983. Abstract Only.

Malik, A. et al., "Sol-Gel Technology for Thermally Stable Coatings in SPME," In Applications of Solid-Phase Microextraction; Royal Society of Chemistry; London, U. K., Chapter 6, pp 73-91, 1999.

Pesek, J. et al., "Electrochromatography in chemically modified etched fused-silica capillaries," Journal of Chromatography, 736, pp. 255-264, 1996.

Pesek, J. et al., "Separation of tetracyclines by high-performance capillary electrophoresis and capillary electrochromatography," Journal of Chromatography, 736, pp. 313-320, 1996.

Pfeffer, W.D. et al., "Electroosmotically driven electrochromatography of anions having similar electrophoretic mobilites by ion pairing," Abstract, Journal of Chromatography, vol. 557, pp. 125-136, 1991. Abstract Only.

Sawada, H. et al., "Preparation of capillary columns coated with linear polymer containing hydrophobic and charged groups for capillary electrochromatography," Electrophoresis., 20, pp. 24-30, 1999.

Swart, R. et al., "Preparation and evaluation of polyacrylate-coated fused-silica capillaries for reversed-phase open-tubular liquid chromatography," Abstract, Journal of Chromatography, vol. 670, pp. 25-38, 1994. Abstract Only.

Tan, Z. et al., "Preparation and Evaluation of Bonded Linear Polymethacrylate Stationary Phases for Open Tubular Capillary Electrokinetic Chromatography," Anal. Chem., 69, pp. 581-586, 1993.

Tsuda, T. et al., "Open-Tubular Microcapillary Liquid Chromatography with Electro-Osmosis Flow Using A UV Detector," Journal of Chromatography, vol. 248, pp. 241-247, 1982.

Van Berkel, et al., "The Application of Immobilized Liquids for Open-Tubular Liquid Chromatography," Chromatographia, vol. 24, pp. 739-744, 1987.

Wang, D., et al., "Sol-Gel Column Technology for Single-Step Deactivation, Coating, and Stationary-Phase Immobilization in High-Resolution Capillary Gas Chromatography," Anal Chem., 69, pp. 4566-4576, 1997.

Zhang, Y. et al., "High Performance Micellar Liquid Chromatography with Silica Micro-Particles Having Surface-Bound Cationic Surfactant Moieties. I. Comparison with Octadecylsilica and Applications to the Separation of Dansyl Amino Acids, Herbicides, and Catecholamines," Journal of Liquid Chromatography, 18, pp. 3373-3396, 1995.

Van Berkel-Geldof, O. et al., "Preparation of silicone-coated 5-25-µm I.D. fused-silica capillary columns for open-tabular liquid chromatography," Journal of Chromatography A, vol. 449, 345-359 (1990). Abstract Only.

Yang, Changming, et al., "Capillary zone electrophoresis of proteins with fused-silica capillaries having polymers and surfactants adsorbed onto surfactant moieties previously covalently bound to the capillary column surface," Electrophoresis, 19, 2278-2284 (1998).

Tsuda, Takao, et al., "Open-tubular microcapillary liquid chromatography with 20-µm I.D. colums," Journal of Chromatography A., vol. 214, Issue 3, 283-290 (1981). Abstract Only.

Tock, PPH., et al., "The Application of Porous Silica Layers in Open Tubular Columns for Liquid Chromatography," Chromatograchia, vol. 24, No. 617-624 (1987).

Ruan, Y. et al., "Preparation and Evaluation of Cross-Linked Polyacrylate Stationary Phases for Open Tubular Liquid Chromatography," Chromatographia, vol. 35, No. 9-12 (1993).

Rebscher, H. et al., A Method for the Experimental Determination of Contributions to Band Broadening in Electrochromatography with Packed Capillaries, Chromatographia, vol. 38, No. 11/12 (1994).

* cited by examiner

SOL-GEL OPEN TUBULAR ODS COLUMNS WITH CHARGED INNER SURFACE FOR CAPILLARY ELECTROCHROMATOGRAPHY

CROSS-RELATED REFERENCE SECTION

This application claims the benefit of priority under 35 U.S.C. Section 119(e) of U.S. Provisional Patent Application No. 60/263,988, filed Jan. 24, 2001, which is incorporated herein by reference.

BACKGROUND OF THE INVENTION

1. Technical Field

The present invention relates to analytical separation technology and more specifically towards capillary electrochromatography.

2. Background Art

Various capillary chromatographic separation techniques exist for analytical separation of various substances, compounds, and solutes. Some examples of capillary chromatographic separation methods include, but are not limited to, high-performance liquid chromatography (hereinafter "HPLC"), capillary gas chromatography, capillary electrochromatography (hereinafter "CEC"), and supercritical chromatography. Specifically, CEC is considered a rapidly growing technique in the area of analytical separations. CEC is a hybrid technique between HPLC and capillary zone electrophorens (CZE). The technique of CEC basically involves packing CZE capillaries with HPLC packing, applying a voltage across the packed capillary, and lining an organo-aqueous electrolyte solution. The applied voltage generates an electroosmotic flow (hereinafter "EOF") across the capillary, wherein the differential partitioning and electrophoretic migration of solutes occur during transportation by the EOF resulting in CEC separation.

The current interest in CEC arises primarily from the enhanced separation efficiencies and peak capacities generated in the electrically driven CEC system over that of its conventional counterpart, the pressure driven HPLC system. Additionally, while CZE is applicable only to the separation of electrically charged analytes, CEC can separate both charged and neutral species. This constitutes a major advantage of CEC over CZE. As in HPLC, the separation in CEC is based upon the analyte's differential interactions between the mobile and stationary phases. The plug-like flow profile generated in CEC is responsible for the enhanced separation efficiencies. The use of CEC as an independent separation technique however, requires effective solution of a number of problems. One major problem lies in the area of column technology. The main focus here is to create CEC columns with stable controllable EDF that will allow fritless operation, and prevent bubble formation during a CEC run.

Sol-gel chemistry is an approach that is very applicable to CEC column technology. Sol-gel chemistry provides a general approach to prepare surface coatings on substrates of various dimensions and configurations. It allows for in situ creation of chemically bonded coatings on both the inner surface of capillaries and tubes, as well as on the outer surface of solid substrates of various shapes and sizes. Sol-gel chemistry is applicable for the preparation of both thin (<1 $\mu$m) and thick (>1 $\mu$m) coatings that possess high operational stability. Additionally, sol-gel chemistry has been successfully used as coatings for separation media located within various separation devices including, but not limited to, open tubular columns with surface-bonded octadecylsilane (hereinafter "ODS") coatings in columns for use in open tubular capillary electrochromatography (hereinafter "OT-CEC"). The use of such sol-gel chemistry in column manufacture improves performance.

As for specific formats, an open tubular format represents a conceptually simple column design in CEC. In this format, a stable surface-bonded coating needs to be created on the inner walls of a capillary to provide efficient chromatographic separation and reliable electroosmotic flow. The OT-CEC capillaries more closely resemble those used in capillary zone electrophoresis (hereinafter "CZE"), therefore commercially available instruments designed for CZE can be used for CEC operations without requiring any instrumental modifications (e.g., pressurization capabilities exist). Furthermore, sample introduction is not limited to the biased electrophoretic mode as the pressurization levels required for hydrodynamic injections are readily achievable when open tubular columns are used. Open tubular columns do not require the use of retaining end-frits and packing materials, and therefore are practically free from bubble formation problems and other technical difficulties associated with the use of packed capillary columns.

OT-CEC columns have been used for various applications. For instance, Tsuda et al. demonstrated the separation of a series of hydrocarbons on ODS coated capillaries. For this, the 30-$\mu$m i.d. soda lime capillaries were first treated with sodium hydroxide, followed by the attachment of the stationary phase using silane chemistry. Bruin and co-workers (Bruin et al.) have used octadecylsilane coated 10–25 $\mu$m i.d. OT-CEC capillaries for the separation of a test mixture of polycyclic aromatic hydrocarbons (PAHs). Using applied voltages of 20 kV and a 1:1 50 mM phosphate/methanol mobile phase, plate height values of 1.2 $\mu$m were obtained for PAHs. Pesek and Matyska also reported the use of $C_{18}$ bonded stationary phases within previously etched 50 $\mu$m i.d. fused-silica capillaries. In these studies, capillary modifications were performed using triethoxysilane, accompanied by a subsequent reaction with octadecene. Test mixtures of proteins and peptides and of tetracyclines were separated using a methanolic mobile phase. Yeung and co-workers (Pfeffer et al. and Garner et al.) added tetrabutylammonium (TBA) to the buffer solution and separated naphthalenesulfonic acid anions on OT-CEC capillaries. Tan and Remcho used a polymethacrylate coating within 25 $\mu$m i.d. capillaries for use in OT-CEC. Prepared through the polymerization of methacrylates, these OT-CEC columns generated efficiencies of up to 270,000 plates/m when separating a mixture of four benzoates.

Sawada et al. recently prepared coated open tubular columns for CEC using a copolymerization of N-tert-butylacrylamide (TBAAm) with 2-acrylamido-2-methyl-1-propanesulfonic acid (AMPS). EOF, essential in CEC, can be generated as a result of the incorporation of the negatively charged AMPS into the chemical structure of the polymeric coating. Columns prepared by this in situ copolymerization technique proved successful for the separation of ketones, parabens, and PAHs. Guo et al. used sol-gel technology to cast a thin film on the inner fused-silica capillary surface for use in OT-CEC. By altering the percentage of octyl moieties, successful separation of a test mixture of five PAHs was achieved.

Despite the simplicity in design and user-friendliness in operation, open tubular columns are not as widely used as the packed capillary or monolithic columns in current CEC practice. This is partially attributed to slow solute diffusion in a liquid mobile phase and to a low sample capacity of the open tubular columns. To undergo interaction with the stationary phase, analytes must travel a significant distance (on a molecular scale) through the mobile phase. Thus, the column internal diameter must be small, the stationary phase film must be thick, and the column length must be great to render sufficient chromatographic interactions in the OT-CEC. To overcome these limitations a number of different approaches have been used in the preparation of open tubular columns.

One of the first published approaches to overcome the above mentioned limitations involved etching the capillary inner surface prior to affixing a chromatographically favorable stationary phase. (Hibi, et al., Jorgenson et al., Ishii et al., and Tsuda et al.). This etching process was primarily employed to increase the surface area of the smooth capillary inner walls, thereby providing favorable phase ratio values. Unfortunately, low retentions and sample capacities were inherent characteristics of columns prepared by this technique.

A second approach to the fabrication of open tubular columns involved first casting a siliceous sub-layer along the inner capillary surface. Again, as in the use of etched surfaces, this layer of silica is used to increase the capillary's inner surface area. Next, a monomeric stationary phase is chemically attached to this sublayer, thus creating a chromatographically favorable coated surface. However, the reproducibility of preparing homogeneous capillaries using this bi-modal technique is poor.

A third approach to the fabrication of open tubular columns involved the use of relatively thick, immobilized, polymeric films to enhance solute sorption. (Van Berkel et al., Folestad et al., van Berkel et al., Gohlin et al. (1991), Gohlin et al. (1993), Jorgenson et al., Ruan et al., Swart et al.). The creation of a cross-linked coating along the inner fused-silica capillary surface quickly gained interest due to the ease of column fabrication. Despite poor solute diffusion rates and stationary-phase bleeding, this technique was often employed for the preparation of open tubular columns for liquid-phase separations.

Accordingly, there is a need for an improved column and method of manufacturing the column thereof wherein increased performance of separation occurs through the use a prepared open tubular column coated with a specific sol-gel solution. Further, there is a need for controlling EOF in order to improve separation of electrically charged and/or neutral analytes by CEC.

SUMMARY OF THE INVENTION

According to the present invention, there is provided a column for use in capillary electrochromatography including a tube, wherein the tube includes an inner surface having a positively or negatively charged, chemically-bonded sol-gel stationary coating thereon. The present invention further provides for a method of making a column for use in capillary electrochromatography, including a tube, wherein the tube includes an inner surface having a positively or negatively charged chemically-bonded sol-gel tationary coating thereon, wherein the steps include filling the column with a sol-gel solution, maintaining the sol-gel solution within the column, and forcing the sol-gel solution out of the column with an inert gas. Further, the present invention provides for a method of analytical separation with a column including an inner layer having a positively charged chemically-bonded sol-gel stationary coating thereon that reverses the direction of electroosmotic flow in the column compared with a column without the positive surface charge. Additionally, the present invention provides for a method of using a column including an inner layer of positively charged chemically-bonded sol-gel stationary coating thereon by introducing a sample into the column and operating under reversed electroosmotic flow due to positively charged chemically-bonded sol-gel stationary coating.

DESCRIPTION OF THE DRAWINGS

Other advantages of the present invention are readily appreciated as the same becomes better understood by reference to the following detailed description when considered in connection with the accompanying drawings wherein.

Figure 8:
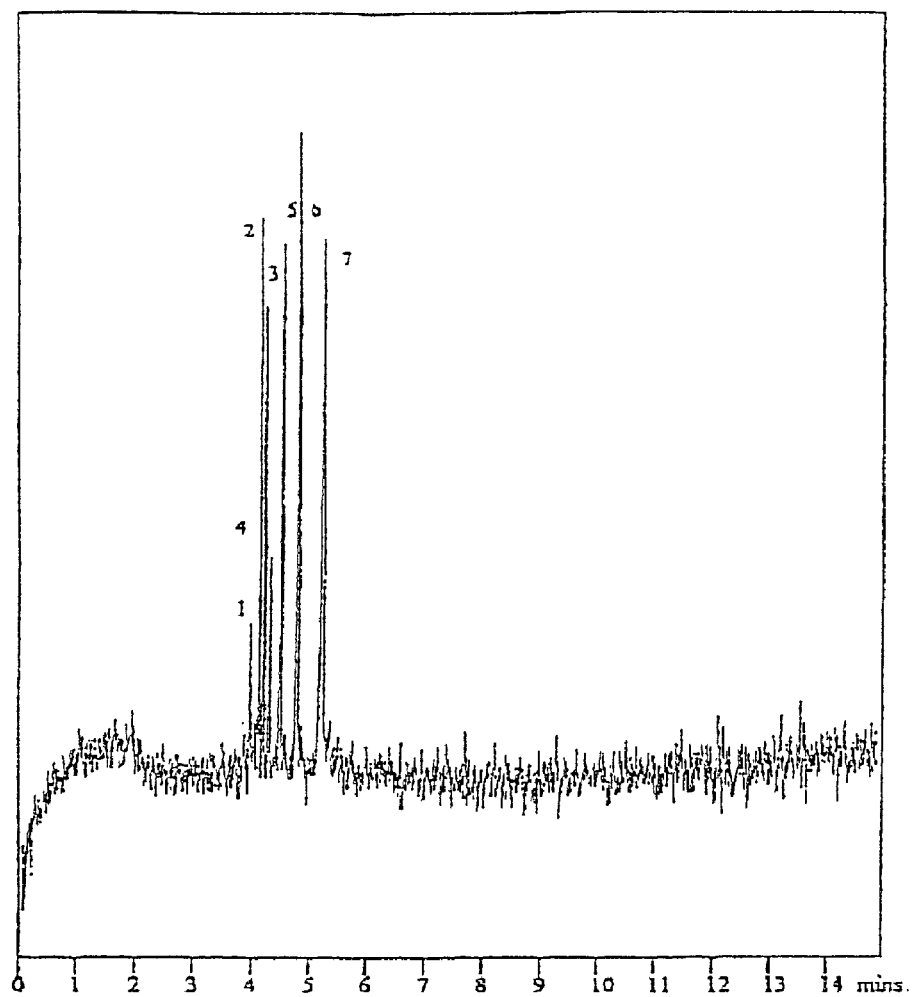
Figure 9:
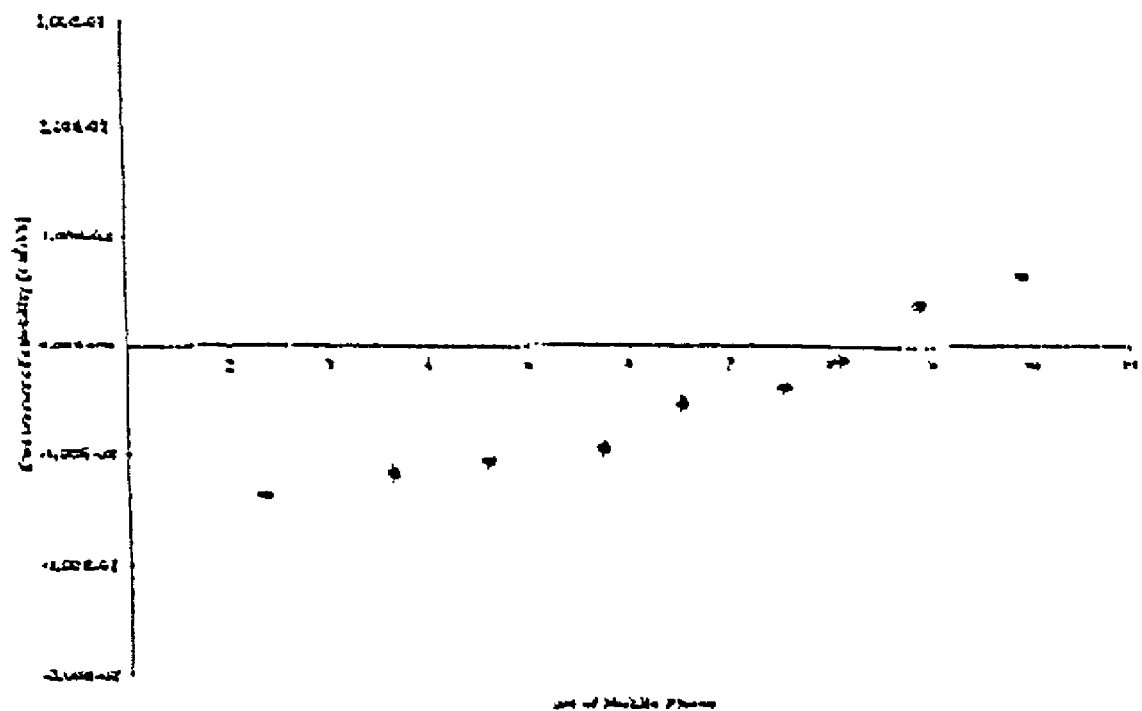

injection 0.04 minutes at 100 mbar; run −25 kV, −0.5 µA. Analyte peaks (in order of elution): (1) thiourea, 7.6×10$^{-3}$ M, N=404,000 plates/m; (2) benzaldehyde, 1.89×10$^3$M, N=232,000 plates/m, k=0.019; (3) tolualdehyde, 3.33×10$^{-3}$ M, N=231,000 plates/m, k=0.030; (4) butyrophenone, 10.61×10$^{-3}$ M, N=28,000 plates/m, k=0.050; (5) valerophenone, 1.06×10$^{-3}$ M, N=218,000 plates/m, k=0.078; (6) hexanophenone, 8.26×10$^{-3}$ M, N=202,000 plates/m, k=0.119; (7) heptanophenone, 7.65×10$^{-3}$ M, N=195,000 plates/m, k=0.181;

FIG. 8 is an OT-CEC separation of a test mixture of benzene derivatives using a PheDMS-deactivated sol-gel $C_{18}$ coated column. Separation conditions: capillary column, 25 µm i.d.×64 cm (inlet to detector); mobile phase 60:40 v/v ACN/Tris-HCl (5 mM, pH 2.34); injection 0.05 minutes at 100 mbar; run −30 kV, −0.7 µA. Analyte peaks (in order of elution): (1) thiourea, 7.6×10$^{-3}$ M, N=384,000 plates/m; (2) benzene, 53.9×10$^{-3}$ M, N=310,000 plates/m, k=0.041; (3) toluene, 56.63×10$^{-3}$M, N=261,000 plates/m. k=0.063; (4) ethylbenzene, 1.97×10$^{-3}$ M, N=246,000 plates/m, k=0.089; (5) propylbenzene, 64.84×10$^{-3}$ M, N=220,000 plates/m, k=0.137; (6) butylbenzene, 77.20×10$^{-3}$ M, N=204,000 plates/m, k=0.208; (7) amylbenzene, 70.12×10$^{-3}$ M, N=209,000 plates/m, k=0.316; and FIG. 9 is an electroosmotic mobility vs electrolyte pH used in the mobile phase using a PheDMS-deactivated sol-gel $C_{18}$ coated OT-CEC column. Separation conditions: capillary column, 25 µm i.d.×64 cm (inlet to detector); mobile phases 50:50 v/v ACN/Tris-HCl (5 mM, pH 2.34–9.91; injection 0.05 minutes at 100 mbar; run −15 kv; EOF marker thiourea, 7.6×10$^{-3}$ M.

DETAILED DESCRIPTION OF THE INVENTION

Figure 1:
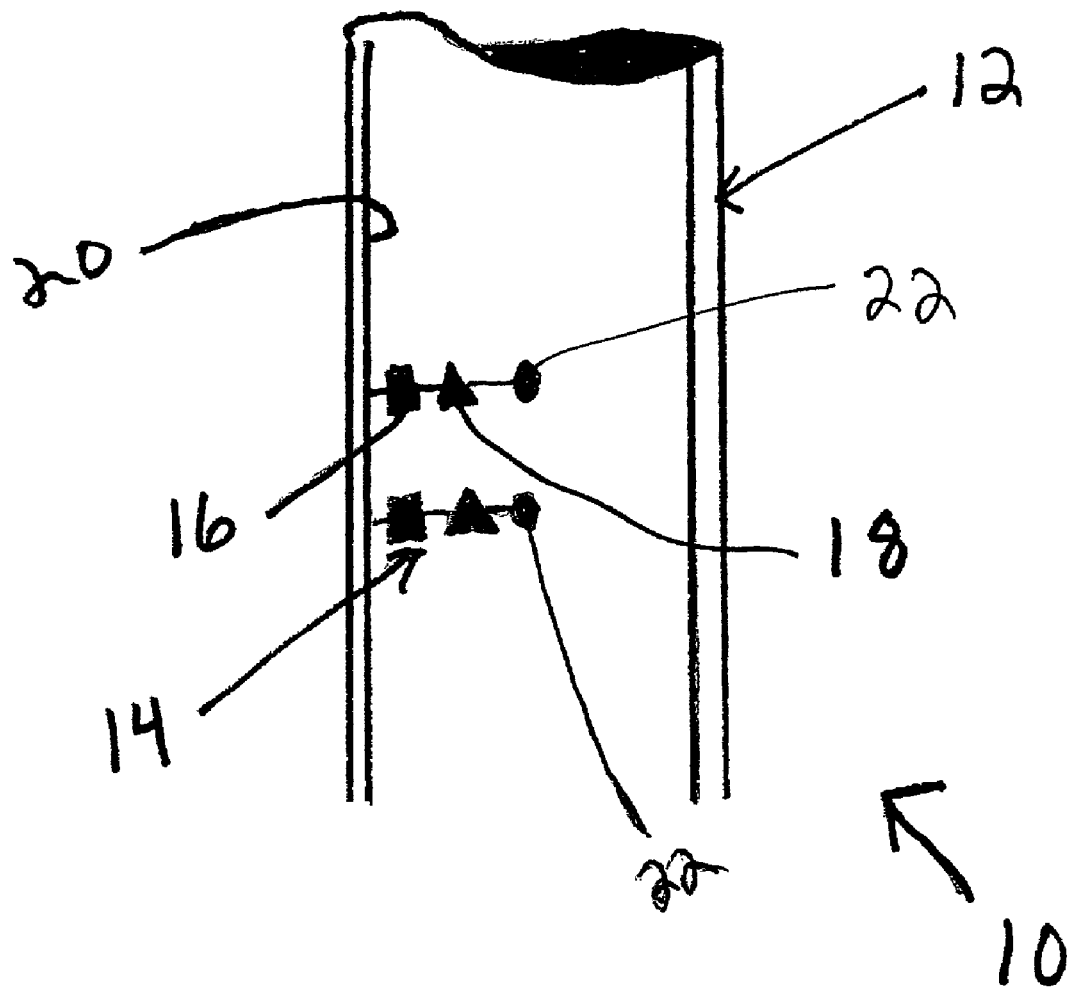
FIG. 1 is drawing of an embodiment of the present invention.

Generally, the present invention provides for novel column 10 having a specific sol-gel coating for use in capillary electrochromatography (FIG. 1). Further, the present invention provides for a novel sol-gel chemistry-based method for coating columns with a specific sol-gel solution in order to create a charged surface-bonded stationary phase coating. Specifically, the column of the present invention includes a tube 12 having an inner surface 20. The inner surface 20 of the tube 12 further has a positively or negatively charged surface-bonded stationary coating 14 that is responsible for high electroosmotic flow. The positively charged surface is responsible for the reversal of EOF direction in the column compared with bare fused silica columns that do not have a positively charged surface. The present invention further provides for a method of making the above-described column. This method includes the steps of filling the column with a sol-gel solution, maintaining the sol-gel solution within the column, and forcing the sol-gel solution out of the column with an inert gas. The present invention also provides for a method of analytical separation and a method for using the column.

The present invention has numerous applications and uses. Primarily, the present invention is useful in separation processes involving electrically charged or neutral analytes including, but not limited to, genetic material, proteins, chemical compounds, ions, organic acids and bases, carbohydrates, and any other similar charged or uncharged analytes known to those of skill in the art. Accordingly, the present invention is useful in pharmaceutical applications, genetic engineering, protein and peptide separations and analysis, clinical and forensic applications, agrochemical analysis, nucleotide separation, DNA analysis and profiling, drug discovery, drug purification, analysis of drugs, chiral pharmaceuticals, carbohydrates, proteins, glycoproteins, and nucleic acids, determining presence of organic acids, and metal ions, collection of protein digest samples, and any other similar applications known to those of skill in the art.

The present invention further provides for many advantages over conventional approaches. First, the sol-gel approach requires significantly less time and effort to prepare an OT-CEC column than is required by conventional approaches to the preparation of open tubular, packed, or monolithic CEC columns. Second, casting a sol-gel stationary-phase coating along the inner surface is much simpler to perform than the fabrication of open tubular, packed, or monolithic capillary columns by conventional methods. With the sol-gel approach, the tedious multi-step processes involved in conventional OT CEC column technology are replaced by a simple procedure. Third, the sol-gel approach of the present invention allows for an effective method of controlling EOF in the column by either adjusting the concentration of the precursor in the sol-gel solution responsible for the positive charge in the surface-bonded stationary coating, or the pH of the background electrolyte.

Generally, the column 10 of the present invention includes a chromatographically favorable coating or substrate 14 (i.e., sol-gel stationary phase) immobilized along the inner capillary surface 20. This coating or substrate 14 renders the essential sorption and/or desorption interactions of the target analytes. The column 10 itself includes a tube made from numerous materials including, but not limited to, fused-silica, glass, titania, zirconia, alumina, polymeric hollow fibers with sol-gel active surface groups, and any other similar tubing materials known to those of skill in the art.

The coating or substrate 14 chemically bonded to the inner surface of the tube 20 is defined as a sol-gel polymer including a positively or negatively charged moiety 18 and a chromatographic ligand 22. The positively charged moiety 18 is a strong base including, but not limited to, quaternary amine groups, Nitrogen, strong inclusion complexes or adducts of cations within cavities of organic or inorganic moieties bonded to the capillary surface, and any other similar strong bases known to those of skill in the art. Some examples of suitable complexes would be copper ion, cobalt ion, nickel ion complexes and any other complexes known to those skilled in the art. As for a negatively charged moiety 18, it is a strong acid including, but not limited to, a sulfonic acid moiety, strong inclusion complexes or adducts of anions, and any other similar strong acids that will provide a negatively charged surface for strong EOF in the normal direction known to those of skill in the art.

The sol-gel polymer 14 is formed from sol-gel moieties or precursors that include sol-gel reactive groups wherein either alkoxy or hydroxyl groups exist for the needed polycondensation reactions between these groups and the silica-containing tubes or other metal oxide tubes. The sol-gel precursors also include an inner metal that includes, but is not limited to, aluminum, titanium, silicon, zirconium, vanadium and any other transition metal. These inner metal atoms become part of the backbone of the resulting sol-gel polymer coating 14.

The sol-gel coating 14 can further include a chromatographically active ligand 22 bonded thereto. The ligand is selected from the group consisting of $C_{18}$, $C_8$, $C_4$, $C_{12}$, $C_{30}$, alkyl chains, octadecyl, octyl, cyanopropyl, diol, biphenyl, phenyl, cyclodextrins, crown ethers, Tetramethoxysilane, 3-(N-styrylmethyl-2-aminoethylamino)-propyltrimethoxysilane hydrochloride, N-tetradecyldimethyl(3-trimethoxysilylpropyl)ammonium chloride, N(3-trimethoxysilylpropyl)-N-methyl-N,N-diallylammonium chloride, N-trimethoxysilylpropyltri-N-butylammonium bromide, N-trimethoxysilylpropyl-N, N, N-trimethylammonium chloride, Trimethoxysilylpropylthiouronium chloride, 3-[2-N-benzyaminoethylaminopropyl]trimethoxysilane hydrochloride, 1,4-Bis(hydroxy-dimethylsilyl)benzene, Bis(2-hydroxyethyl)-3-aminopropyltriethoxysilane, 1,4-bis(trimethoxysilylethyl)benzene, 2-Cyanoethyltrimethoxysilane, 2-Cyanoethyltriethoxysilane, (Cyanomethylphenethyl)trimethoxysilane, (Cyanomethylphenethyl)triethoxysilane, 3-Cyanopropyl-dimethylmethoxysilane, 3-Cyanopropyltriethoxysilane, 3-Cyanopropyltrimethoxysilane, n-Octadecyltrimethoxysilane, n-Octadecyidimethylmethoxysilane, Methyl-n-Octadecyidiethoxysilane, Methyl-n-Octadecyldimethoxysilane, n-Octadecyltriethoxysilane, n-Dodecyl-triethoxysilane, n-Dodecyltrimethoxysilane, n-Octyltriethyoxysilane, n-Octyltrimethoxysilane, n-Ocyidi-isobutylmethoxysilane, n-ctylmethyidimethoxysilane, n-Hexyltriethoxysilane, n-isobutyltriethoxysilane, n-Propyltrimethoxysilane, Phenethyltrimethoxysilane, N-Phenylaminopropyltrimethoxysilane, Styrylethyl-trimethoxysilane, 3-(2,2,6,6-tetramethylpiperidine-4-oxy)-propyltriethoxysilane, N-(3-triethoxysilyl-propyl)acetyl-glycinamide, (3,3,3-trifluoropropyl)trimethoxysilane, (3,3,3-trifluoro-propyl)methyl-dimethoxysilane, 3-mercaptopropyltrimethoxysilane, 3-mercaptopropyltriethoxysilane, mercaptomethylmethyldiethoxysilane, 3-mercaptopropylmethyidimethoxysilane, 3-mercaptopropyloctadecyldimethoxysilane, 3-mercaptopropylloctyldimethoxysilane, 3-mercaptopropylcyanopropyldimethoxysilane, 3-mercaptopropyloctadecyldiethoxysilane, and any other similar precursor known to those of skill in the art. For instance, in one embodiment, the sol-gel precursor utilized is N-octadecyldimethyl[3-trimethoxysilyl)propyl]ammonium chloride (hereinafter "$C_{18}$-TMS"). When the sol-gel polymer gets bonded to the capillary walls, the quaternary amine group in the precursor provides positive surface charge, while the octadecyl ligand in the surface coating coming from the precursor is capable of providing chromatographic interaction with the analytes. Thus, the sol-gel polymer forms an octadecylated sol-gel coating chemically bonded to the inner surface of the capillary. Thus, the resulting coating may contain residual silanol groups that need to be deactivated. In order to deactivate the stationary phase coating, a deactivating reagent such as phenyldimethylsilane (PheDMS) is added to the sol-gel solution. The deactivation can take place during a thermal treatment step, which is carried out following the sol-gel coating procedure.

As described above, in addition to having a charged chemically-bonded stationary coating 14, the columns 10 of the present invention have sol-gel moieties that allow for the chemically bonding of the coating to the inner surface of the tube. The sol-gel moiety is made from various sol-gel precursors. In one embodiment of the present invention, the reagent system that is utilized for the fabrication of the coating includes two sol-gel precursors, a deactivation reagent, one or more solvents and a catalyst. For the purposes of the present invention, one of the sol-gel precursors contains a chromatographically active moiety selected from the group consisting of octadecyl, octyl, cyanopropyl, diol, biphenyl, phenyl, cyclodextrins, crown ethers and other moieties. Representative precursors include, but are not limited to: Tetramethoxysilane, 3-(N-styrylmethyl-2-aminoethylamino)-propyltrimethoxysilane hydrochloride, N-tetradecyidimethyl(3-trimethoxysilylpropyl)ammonium chloride, N(3-trimethoxysilylpropyl)-N-methyl-N,N-diallylammonium chloride, N-trimethoxysilylpropyltri-N-butylammonium bromide, N-trimethoxysilylpropyl-N,N,N,-trimethylammonium chloride, Trimethoxysilylpropylthiouronium chloride, 3-[2-N-benzyaminoethylaminopropyl]trimethoxysilane hydrochloride, 1,4-Bis(hydroxy-dimethylsilyl)benzene, Bis(2-hydroxyethyl)-3-aminopropyltriethoxysilane, 1,4-bis(trimethoxysilylethyl)benzene, 2-Cyanoethyltrimethoxysilane, 2-Cyanoethyltriethoxysilane, (Cyanomethylphenethyl)trimethoxysilane, (Cyanomethylphenethyl)triethoxysilane, 3-Cyanopropyl-dimethylmethoxysilane, 3-Cyanopropyltriethoxysilane, 3-Cyanopropyltrimethoxysilane, n-Octadecyltrimethoxysilane, n-Octadecyidimethylmethoxysilane, Methyl-n-Octadecyldiethoxysilane, Methyl-n-Octadecyldimethoxysilane, n-Octadecyltriethoxysilane, n-Dodecyl-triethoxysilane, n-Dodecyltrimethoxysilane, n-Octyltriethyoxysilane, n-Octyltrimethoxysilane, n-Ocyldi-isobutylmethoxysilane, n-ctylmethyldimethoxysilane, n-Hexyltriethoxysilane, n-isobutyltriethoxysilane, n-Propyltrimethoxysilane, Phenethyltrimethoxysilane, N-Phenylaminopropyltrimethoxysilane, Styrylethyl-trimethoxysilane, 3-(2,2,6,6-tetramethylpiperidine-4-oxy)-propyltriethoxysilane, N-(3-triethoxysilyl-propyl)acetyl-glycinamide, (3,3,3-trifluoropropyl)trimethoxysilane, (3,3,3-trifluoro-propyl)methyl-dimethoxysilane, 3-mercaptopropyltrimethoxysilane, 3-mercaptopropyltriethoxysilane, mercaptomethylmethyldiethoxysilane, 3-mercaptopropylmethyidimethoxysilane, 3-mercaptopropyloctadecyldimethoxysilane, 3-mercaptopropylloctyldimethoxysilane, 3-mercaptopropylcyanopropyldimethoxysilane, 3-mercaptopropyloctadecyidiethoxysilane, and any other similar precursor known to those of skill in the art.

As for the deactivation reagent, phenyldimethylsilane, and the catalyst, trifluoroacetic acid, they are selected for the preparation of the columns of the instant invention. However, any deactivation reagent and/or catalyst as known to those of ordinary skill in the art can be used.

As previously mentioned, one embodiment of the present invention utilizes the quaternary amine group of $C_{18}$-TMS. This group possesses a chromatographically favorable, bonded ODS moiety, in conjunction with three methoxy groups allowing for sol-gel reactivity. In addition, a positively charged nitrogen atom is present in the molecular structure of this reagent and provides the positively charged capillary surface responsible for the reversed EOF in the columns during CEC operation. Thus, using $C_{18}$-TMS as a sol-gel precursor, a positively charged surface coating can be along the inner walls of the columns. The sol-gel created positively charged surface of the column of the present invention has a pi value of 8.5 and is responsible for the observed reversal of EOF in such sol-gel coated columns in CEC when the mobile-phase pH crosses this value.

In another embodiment of the present invention, a method of making the described column is provided. The sol-gel method of coating the open tubular column with a surface-bonded sol-gel stationary phase simply involves filling a capillary substrate such as fused-silica with a properly designed sol solution and maintaining the sol solution within the capillary for a short period of residence time (e.g., 15 to 30 minutes) to allow for chemical bonding of the growing sol-gel polymer to the capillary inner walls. Afterwards, expulsion of the unbounded surface part of the sol solution under an inert gas pressure occurs. Moreover, the coated capillary is further thermally treated and rinsed with a series of solvents before use.

In the presented sol-gel approach, a single step process is used to in situ create a chromatographically favorable stationary-phase coating chemically bonded to the inner walls of the fused-silica capillary. One associated advantage to this particular technique originates from the use of a selectively chosen, commercially available sol-gel precursor, $C_{18}$-TMS. The chemical structures of this reagent, and other ingredients used for the fabrication of the sol-gel coatings are given in Table 1. As depicted in Table 1, the chemical architecture of $C_{18}$-TMS elegantly combines three important features: (1) three methoxysilyl groups that can undergo sol-gel reactions and in situ create a chemically bonded stationary phase in the form of a surface coating; (2) the octadecyl chain that remains chemically bonded to the sol-gel surface coating as a pendant group to provide the essential chromatographic interactions with the solute molecules; (3) the positively charged quaternary ammonium moiety that provides positively charged sites on the coated surface to support reversed electroosmotic flow (i.e. from cathode to anode) in the capillary electrochromatographic columns. Previously, this reagent was used by Yang and El Rassi to create a cationic surfactant moiety (hereinafter "CSM") coated sublayer. A hydrophilic surfactant (e.g. Brij 35, hydroxypropylcellulose (hereinafter "HPC") was then adsorbed atop the CSM sublayer for use in capillary zone electrophoresis (Yang et al.) and high-performance liquid chromatography (Zhang et al.). Recently, we have successfully used this reagent as a sol-gel precursor to create monolithic columns with reversed electroosmotic flow for use in CEC. (Hayes et al.). In principle, a sol-gel precursor with a negatively charged moiety (e.g., a sulfonic acid group) in its structure can be used as well to create a negatively charged surface coating to provide normal EOF (i.e., from the anode to the cathode). This can be achieved by using a thiol-containing sol-gel precursor (e.g., 3-mercaptopropyloctadecyldimethoxysilane). After coating, the sol-gel surface containing thiol groups can be treated with hydrogen peroxide in an acidic medium to convert the thiol groups into sulfonic acid groups to provide negative charge to the coating.

Sol-gel precursors can undergo hydrolytic polycondensation. The hydrolytic polycondensation reactions undergone by the sol-gel precursors (Brinker et al.) provide a unique, yet simple and effective pathway for the fabrication of open tubular CEC columns. In one embodiment, tetramethoxysilane and $C_{18}$-TMS are the two sol-gel precursors selected. The first step of the sol-gel process involves the hydrolysis of the precursor(s). The hydrolysis reaction, undergone by both precursors, involves the nucleophillic attack by a water molecule on the silicon atom of the precursor, replacing the methoxy substituents with hydroxy moieties. The hydrolysis of $C_{18}$-TMS is illustrated in Scheme 1.

As the sol-gel reactions proceed, the products of hydrolysis undergo polycondensation reactions in a variety of ways: (a) between the hydrolyzed products of the same original precursor; (b) between hydrolyzed products of two different types of precursors; (c) between the hydrolyzed products of either precursor and the silanol or alkoxy group on the growing sol-gel network; (d) between the silanol groups on the inner capillary surface and sol-gel reaction products in their vicinity. It can be assumed that the creation of a surface-bonded sol-gel coating will involve different combinations of all these reactions. A simplified condensation reaction between the hydrolysis products of both precursors is depicted in Scheme 2.

The condensed products can then undergo further condensation reactions with other sol-gel active species in the sol solution to create a three-dimensional sol-gel network. The sol-gel network growing in the vicinity of the capillary walls can eventually become anchored to the inner capillary surface through chemical bonding with the silanol moieties residing along the inner fused-silica capillary surface. Sol-gel-active moieties, present on the hydrolyzed products of $C_{18}$-TMS or their condensation products with other hydrolyzed sol-gel active moieties can undergo chemical binding with the silanol groups along the capillary inner surface. Scheme 3 represents the simplified representations of condensation reactions of both types occurring with the inner fused-silica surface.

In another embodiment of the present invention, a method of manufacturing the column described herein is provided. Preparation of the sol-gel open tubular CEC capillary columns involves the following two major steps: (1) hydrothermal treatment of the inner fused-silica capillary surface and (2) sol-gel coating of the capillary inner surface. Hydrothermal treatment of the fused-silica capillary inner-surface begins with treatment of the inner-surface thereof with deionized water. This initial hydrothermal treatment is performed for several reasons. First, the water serves to clean the inner capillary surface, removing any contaminants originating from the capillary drawing process or postdrawing manipulation and handling. Moreover, this pretreatment with water enhances surface silanol concentrations, thereby offering a higher percentage of bonding sites for anchoring the sol-gel coating.

Addition of phenyldimethysilane (PheDMS) to the sol-gel solution is responsible for subsequent deactivation of the stationary phase coating on the inner capillary surface. The deactivation takes place during a thermal treatment step, which is carried out following the sol-gel coating procedure. To accomplish deactivation of a sol-gel ODS coated capillary, PheDMS was added to the sol-gel solution. This deactivating reagent is capable of chemically reacting with the silanol groups on the coated surface, thereby reducing the number of active residual silanol moieties on the original fused-silica capillary surface or on the sol-gel coating. An example of PheDMS deactivation process occurring on the sol-gel coating is illustrated in Scheme 4.

In operation, the sol-gel OT-CEC columns of the present invention are initially equilibrated with the running mobile phase. A series of EOF measurements are performed to evaluate the magnitude and direction of EOF, which, in turn, is determined by the magnitude and sign of charge on the inner surface of the open tubular columns. It is logical to anticipate that the magnitude and direction of EOF in the prepared columns with quanternary amine groups is determined by the relative contributions of positively charged quaternary ammonium moieties anchored to the surface coating and by the negative surface charge due to deprotonated silanol groups. The negative surface charge resulting from the deprotonation of residual silanol groups generate cathodic EOF (directed from anode to cathode), while the positive charge on the coatings is responsible for anodic EOF in the opposite direction. The resultant EOF is in the direction of the greater of these two opposing flows.

Thus, the sol-gel chemistry-based method that is disclosed herein for the preparation of ODS coated columns for open tubular CEC is an important advancement in analytical separation technology. Chemical reactions conducted on the inner surface of a hydrothermally treated fused-silica capillary using a sol solution containing appropriate concentrations of two precursors (TMOS and $C_{18}$-TMS), a sol-gel catalyst (TFA), and a surface deactivation reagent (PheDMS) leads to the in situ creation of a surface-bonded inorganic-organic coating with ODS ligands. The quarternary ammonium moiety in $C_{18}$-TMS provided positive charge to the sol-gel coating on the fused-silica capillary surface and was responsible for relatively high electroosmotic flow in the anodic direction under low pH conditions. EOF versus pH studies showed that sol-gel $C_{18}$ coated columns are characterized by switchable electroosmotic flow in the direction of the cathode at pH values above 8.5, while at pH values below 8.5 it is in the reversed direction. This clearly shows that the created sol-gel $C_{18}$ coating is characterized by an isoelectric point of ~8.5. Separation efficiencies of over 400,000 theoretical plates/m were achieved using the sol-gel ODS columns. The incorporation of a deactivating reagent, PheDMS, into the sol solution proved to be important as capillaries prepared with its use provided enhanced chromatographic efficiency and selectivity over similar columns but lacking deactivation. The excellent chromatographic performance, ease of fabrication, and feasibility of operation in the CEC mode makes the open tubular CEC columns with sol-gel stationary-phase coatings a viable alternative to CEC using packed or monolithic columns.

The above discussion provides a factual basis for the present invention. The methods used with a utility of the present invention can be shown by the following non-limiting examples and accompanying figures.

EXAMPLE

The following example specifically provides for the specific methods and materials utilized with the present invention.

Materials

Fused-silica tubing of 25 μm i.d. is purchased from Polymicro Technologies (Phoenix, Ariz.). Deionized water, ~18 MΩ, which is used for the preparation of electrolyte solutions and for column rinsing, is acquired from a Barnstead model 04741 Nanopure deionized water system (Barnstead/Thermodyne, Dubuque, Iowa., USA). Eppendorf microcentrifuge tubes (1.5 mL) are purchased from Brinkman Instruments (Westbury, N.Y.). HPLC grade acetonitrile and methanol are purchased from Fisher Scientific (Pittsburgh, Pa.). Tetramethyl orthosilicate (99+%), trifluoroacetic acid (99%), thiourea (99.9%), anthracene (99%), valerophenone (99%), butyrophenone (99+%), benzaldehyde (99+%), o-tolualdehyde (97%), and heptanophenone (98%) are all purchased from Aldrich (Milwaukee, Wis.). Tris (hydroxymethyl)aminomethane hydrochloride (reagent grade) that is used in the preparation of background electrolyte solutions, is purchased from Sigma (St. Louis, Mo.).

Adjustments of pH of the electrolyte solutions are achieved through the addition of concentrated hydrochloric acid, or 0.1 M sodium hydroxide solution, prepared using (99.99%) pellets purchased from Aldrich. Various test solutes including, but not limited to, benzene, toluene, ethylbenzene, propylbenzene, butylbenzene, anylbenzene, and naphthalene are from Aldrich. N-octadecyldimethyl[3-(trimethoxysiyl)-propl]ammonium chloride and phenyldimethylsilane are purchased from United Chemical Technologies, Inc. (Bristol, Pa.). Sample vials (300 μL) that are used in all OT-CEC experiments, are from Alltech Associates (Deerfield, Ill.).

Various equipment is utilized with the present invention. All OT-CEC experiments are performed on an ATI Unicam model Crystal 310 capillary electrophoresis system equipped with an ATI Unicam model 4225 variable-wavelength UV detector (Analytical Technology Inc., Boston, Mass.). All OT-CEC data are collected and integrated using ChromPerfect software (Justice Laboratory Software, Mountain View, Calif.). A Microcentaur model APO 5760 centrifuge (Accurate Chemical and Scientific Corp., Westbury, N.Y.) is utilized for necessary centrifugation. A Fisher model G-560 Vortex Genie 2 system (Fisher Scientific) is used for thorough mixing of the sol solutions. A Chemcadet model 5984-50 pH meter (Cole-Palmer Instrument Co., Chicago, Ill.) equipped with a TRIS-specific pH electrode (Sigma-Aldrich, St. Louis, Mo.) is used to measure the pH of the buffers used in the running background electrolyte solutions.

In this particular example, initial preparation of a sol-gel solution begins with the addition of appropriate amounts of two sol-gel precursors (tetramethoxysilane (TMOS) and $C_{15}$-TMS), two different types of trifluoroacetic acid (TFA) reagents containing 1% and 10% water respectively, and PheDMS. As previously mentioned, the later two reagents (e.g., TFA reagents containing 1% and 10% water respectively and PheDMS) serve as the sol-gel catalyst and deactivation reagent, respectively. In the initial experiments, however, PheDMS is not incorporated into the sol solution. This variation allows for the evaluation of the effects of the PheDMS in deactivating OT-CEC capillaries. In the initial experiments, desired volumes (100 μL) of TMOS and of $C_{18}$-TMS (with a molar ratio of 4.26) are added to 100 μL of TFA reagent containing 1% water and 100 μL of TFA reagent containing 10% water. Later experiments also involved the use of 10 μL of PheDMS in the sol solution. This mixture is then thoroughly vortexed for 5 minutes and the precipitate is separated from the sol-gel solution through centrifugation at 13,000 rpm (15682 g) for five minutes. The supernatant is decanted into another microvial and is used for coating the capillaries.

Preparation of the sol-gel open tubular CEC capillary columns involves the following two major steps: (1) hydrothermal treatment of the inner fused-silica capillary surface and (2) sol-gel coating of the capillary inner surface. Hydrothermal treatment of the fused-silica capillary inner-surface begins with treatment of the inner-surface thereof with deionized water. To accomplish this, a ~3 m section of 25 μm-i.d. fused-silica capillary is obtained. Deionized water is then passed through the capillary under helium pressure (200 psi) for ~15 minutes. This is followed by purging of the capillary with helium for five minutes. Both capillary ends are then fused using an oxyacetylene torch and the capillary is placed in a GC oven for thermal conditioning. The conditions for thermal treatment include, for example, an initial temperature of 40° C., with a temperature programming rate of approximately 0.5° C./minutes, and a final temperature of 250° C. (hold time of 60 minutes at 250° C.). Afterward, the column is removed from the GC oven, capillary ends are cut open, and the column is further purged with helium for an additional 30 minutes at ambient temperature.

The steps for sol-gel coating the capillary inner surface occurs by first installing the proximal end of a hydrothermally treated 55 cm×25 μm i.d. fused-silica capillary into a capillary filling or purging chamber (Hayes, J. D. and Malik, A. J. Chromatogr. B, 1997, 695, 3–13). This proximal capillary end is then inserted into a microvial containing the sol-gel solution. Using helium pressure, e.g. 80 psi the sol-gel solution is forced into the capillary. The capillary is filled with the sol-gel solution, and this solution is allowed to remain inside the capillary for 20 minutes to allow sol-gel reactions to occur. Afterwards, the vial containing the sol-gel solution is removed from the capillary filling or purging chamber and the liquid content of the capillary is expelled under helium pressure. The column is further purged under 40 psi helium pressure for an additional 30 minutes.

Column conditioning occurs by first removing the column from the filling or purging chamber. The ends of the column are then sealed using an oxyacetylene torch or other similar heating device known to those of skill in the art. Next, the column is placed in a GC oven for thermal conditioning. The conditions for thermal treatment include, for example, an initial temperature of 40° C., with a temperature programming rate of 0.5° C./minutes, and a final temperature of 150° C. (hold time of 120 minutes at 150° C.). Following thermal treatment, the sealed capillary ends are cut open using an alumina wafer or other cutting tool, and the column is reinstalled into the capillary filling/purging chamber for rinsing. Initially, the columns are rinsed with 100% acetonitrile, followed by 50:50 acetonitrile/deionized wafer solution, and finally the desired running mobile phase.

In order to verify the presence and visualize the sol-gel coatings within the capillary, scanning electron microscopic (hereinafter "SEM") investigations are conducted on several capillary segments. SEM is used for the characterization of coatings in the prepared sol-gel OT-CEC columns. All scanning electron micrographs are obtained using a JEOL JSM-840 SEM or any other similar SEM known to those of skill in the art. The SEM is operated at approximately 15 kV and with a filament current of approximately 60 mA. The samples are acquired from sections of the OT-CEC capillary initially cut into equal lengths (~2.5 cm) and positioned longitudinally within a retractable aluminum stage. These samples are used to depict the surface view of the sol-gel coating from a longitudinal section of the open tubular column. This stage, with the mounted capillary segments, is then placed into a Balzers SCD 050 sputter coating chamber or similar sputter coating device and coated with a gold/palladium alloy at 40 mA for 60 seconds to avert subsequent charging.

Because the fused-silica capillary inner diameter is ~25 μm, which is found to be too small to achieve a cross-sectional view of the capillary using the scanning electron microscopy equipment, generation of a surface view of the coating using a longitudinal section of the coated capillary is performed instead. The initial step involved obtaining small sections (e.g., ~5 cm) of the coated capillary by using an alumina wafer as a cutting tool. These segments are then longitudinally affixed atop aluminum stages and a polymeric mold is cast. Next, the stages containing the capillary segments and polymeric mold are placed in an oven for overnight curing at approximately 100° C. Each stage is then carefully positioned on a mechanical grinder to slowly remove small layers of the polymeric mold. During these steps, a portion of the capillary wall is also carefully removed thereby exposing the coated structure attached to the bottom capillary inner surface.

Figure 2:
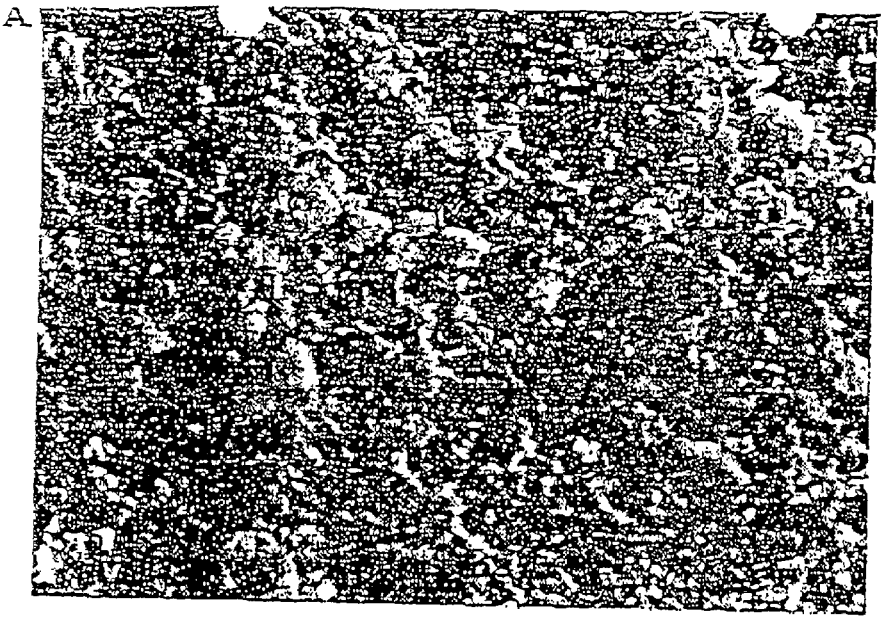
FIG. 2 is a scanning electron micrographs of a sol-gel ODS coated surface inside a fused-silica capillary (surface view of a longitudinal section). Magnification: 20000× (A) and 50000× (B)
Figure 2:

FIG. 2A represents a SEM surface view of a sol-gel coating acquired from a longitudinal section of such a capillary segment at a magnification of 20,000×. Meanwhile, FIG. 2B shows the SEM image of the same sol-gel coated surface at a magnification of 50,000×. These SEM images reveal that the sol-gel coated inner surface of the fused-silica capillary possesses a roughened texture. This surface texture provides enhanced surface area and a favorable environment inside the column for solute-stationary phase interaction.

Evaluation of EOF in the sol-gel OT-CEC columns of the present invention is conducted using DMSO as an EOF marker and a series of mobile phases with varying proportions of organic or aqueous components in the mobile phase. The objective of this series of experiments is to investigate and compare the effects of mobile-phase organic modifier (acetonitrile or methanol) concentration on EOF within uncoated and sol-gel $C_{18}$ coated fused-silica capillary columns. For this, acetonitrile or methanol is used in combination with a 5 mM Tris-HCl (pH 2.34) as the mobile phase. As evident in FIG. 3A, B only negligible differences in EOF are observed when an uncoated 25 μm-i.d. OT-CEC capillary is used with mobile-phase systems containing either acetonitrile or methanol as the organic modifier. Over the entire range of mobile-phase compositions studied, the magnitude of EOF remained positive, which is indicative of a negatively charged surface and an EOF from the anode to cathode. Negligible change in EOF also indicates that, on an uncoated capillary, the surface charge (the determining factor for the magnitude and direction of EOF) practically remains unaffected by the change in the organic modifier content in the mobile phase.

It is evident from FIG. 3C, D that the sol-gel ODS coated column is characterized by reversed EOF. Moreover, a comparison of the magnitudes of EOF for an uncoated and a sol-gel coated capillary clearly demonstrates a significantly stronger EOF on the sol-gel ODS coated column, which is important from an electrochromatographic point of view. Contrary to the results obtained with the uncoated capillary, for a sol-gel coated $C_{18}$ column, the magnitude of EOF is shifted toward higher negative values as the percentage of organic modifier in the background electrolyte is increased. A stronger reversed EOF is obtained for the mobile phase using methanol as the organic modifier in the mobile phase. Experimental results on EOF for bonded ODS particle-packed CEC capillaries using these two mobile-phase systems have been reported in the literature. (Dittman et al., Rebscher et al.). In the present study, however, the direction of flow is reversed due to the positively charged surface and accounts for the differences observed. The observed EOF behaviors can be explained on the basis of differences in the viscosities and dielectric constants of the two organic solvents and changes of the ξ potential throughout the $C_{18}$ coated capillary surface.

Figure 4:
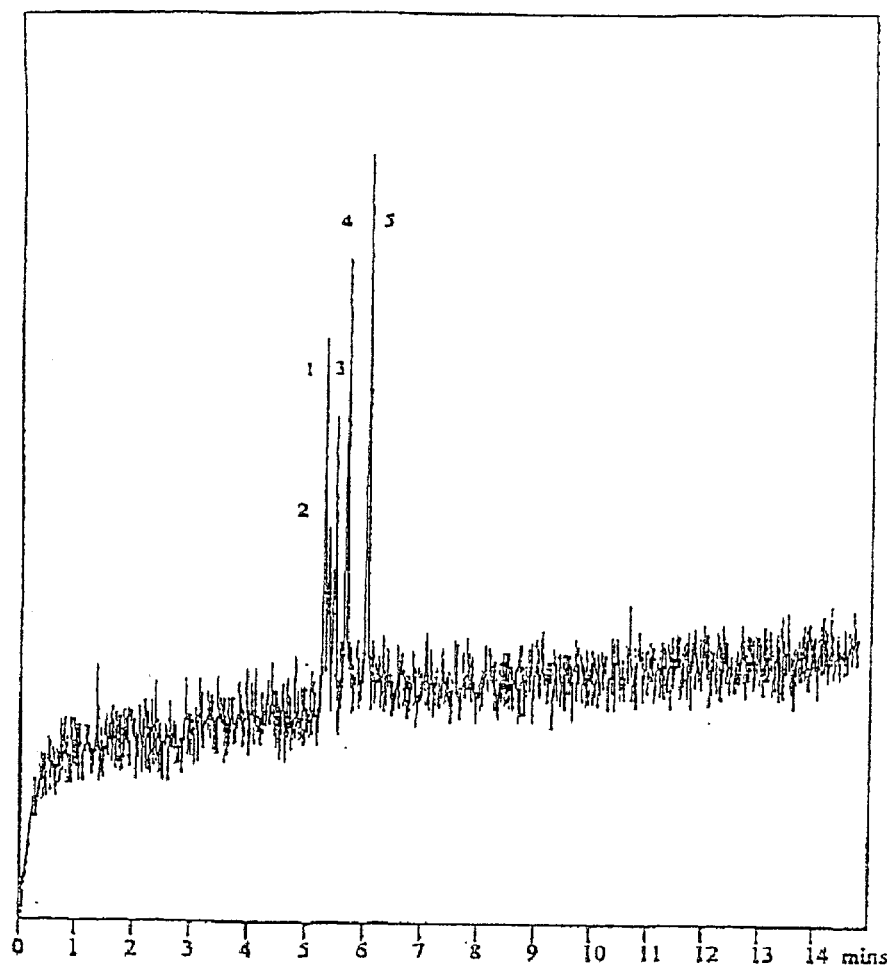
FIG. 4 is an OT-CEC separation of a mixture of PAHs using a sol-gel $C_{18}$ coated open tubular column without deactivation, Separation conditions: capillary column, 25 $\mu$m i.d.×70 cm (inlet to detector); mobile phase 65:35 v/v ACN/Tris-HCl (5 M, pH 2.30); injection 0.04 minutes at 100 mbar; run −25 kV, −0.4 $\mu$A. Analyte peaks (in order of elution): (1) thiourea, 7.6×10$^{-3}$ M, N=155,000 plates/m; (2) benzene, 53.9×10$^{-3}$ M, N=146,000 plates/m; (3) naphthatene, 2.70×10$^{-6}$M, N=201,000 plates/m; (4) anthracene, 9.71×10$^{-7}$ M, N=162,000 plates/m; (5) fluoranthene, 1.20×10$^{-6}$ M, N=172,000 plates/m.

Chromatographic characterization of sol-gel ODS columns in OT-CEC is performed. In the first series of experiments, evaluation of a 25 μm-i.d. sol-gel ODS coated column prepared without the use of a deactivating reagent, PheDMS, in the sol solution is performed. A mixture of four PAHs is the first test probe that is a baseline separated into individual components using a mobile phase including 65% acetonitrile and 35% 5 mM Tris-HCl (pH 2.3) background electrolyte (FIG. 4). The highest column efficiency obtained in this analysis is 201,000 plates/m for naphthalene.

Figure 5:
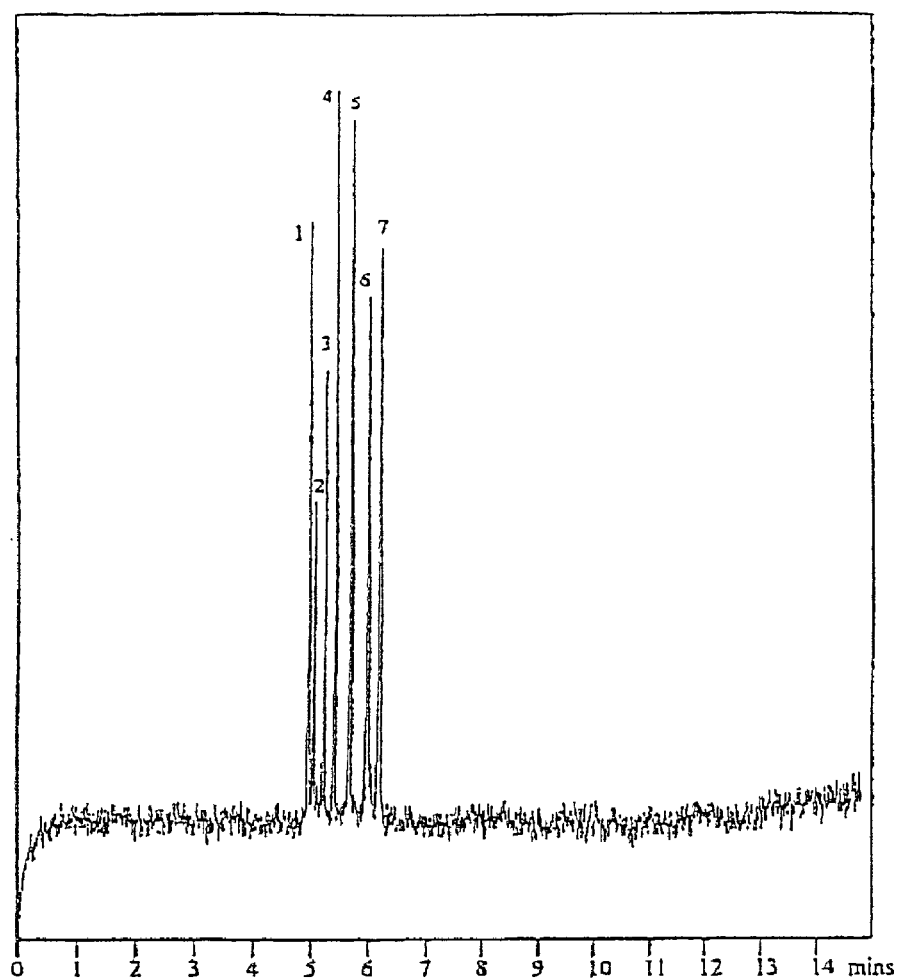
FIG. 5 is an OT-CEC separation of a mixture of PAHs using a PheDMS-deactivated sol-gel $C_{18}$ coated open tubular column. Separation conditions: capillary column, 25 $\mu$m i.d.×64 cm (inlet to detector); mobile phase 70:30 v/v ACN/Tris-HCl (5 mM, pH 2.34); injection 0.04 minutes at 100 mbar; run −25 kV −0.5 $\mu$A. Analyte peaks (in order of elution): (1) thiourea, 7.6×10$^{-3}$ M, N=360,000 plates/m: (2) benzene, 53.9×10$^{-3}$ M, N=266,000 plates/m K=0.018; (3) naphthalene, 2.71×10$^{-6}$ M, N=267,000 plates/m, k=0.056; (4) fluorene, 1.54×10$^{-6}$ M, N=383,000 plates/m, k=0.092; (5) anthracene, 9.69×10$^7$ M, N=268,000 plates/m, k=0.148; (6) Fluoranthene, 1.17×10$^{-6}$ M, N=194,000 plates/m, k=0.206; (7) pyrene, 1.23×10$^{-6}$ M, N=203,000 plates/m, k=0.25.

For comparison, a second OT-CEC column of the same diameter is prepared using PheDMS as a deactivating reagent. This column is fabricated using the same procedure, except that 10 μL of PheDMS is incorporated into the sol solution prior to filing the capillary. Similar to experiments performed on a nondeactivated sol-gel ODS column, a mixture of PAHs is used as a test probe for the PheDMS-deactivated sol-gel ODS column. The evaluation of the separation results allow for a conclusion regarding the effects of deactivation. For this mixture, the highest separation efficiency obtained on the PheDMS-deactivated sol-gel $C_{18}$ coated column is 383,000 theoretical plates/m for a longer retained solute, fluorine (Table 2). This higher efficiency (compared with 201,000 plates/m obtained on a nondeactivated sol-gel ODS column for a less retained solute, naphthalene) is considered as a direct consequence of column deactivation. Besides higher separation efficiency, the PheDMS deactivation also provides better resolution and allows for the use of a mobile phase containing a higher percentage of organic modifier. FIG. 5 depicts the analysis results of a test mixture of PAHs on a PheDMS-deactivated sol-gel ODS column.

The run-to-run repeatability of the sol-gel OT-CEC columns are illustrated by experimental retention data for two classes of compounds: aromatic hydrocarbons (Table 2) and aromatic carbonyl compounds (Table 3). As can be seen in nine replicate runs, the sol-gel OT-CEC columns provide a relative standard deviation (RSD) of less than 0.70%. For the carbonyl compounds, an RSD value of less than 0.80% is observed for five replicate runs. Both of these values are indicative of a high degree of retention time repeatability on sol-gel OT-CEC columns.

Figure 6:
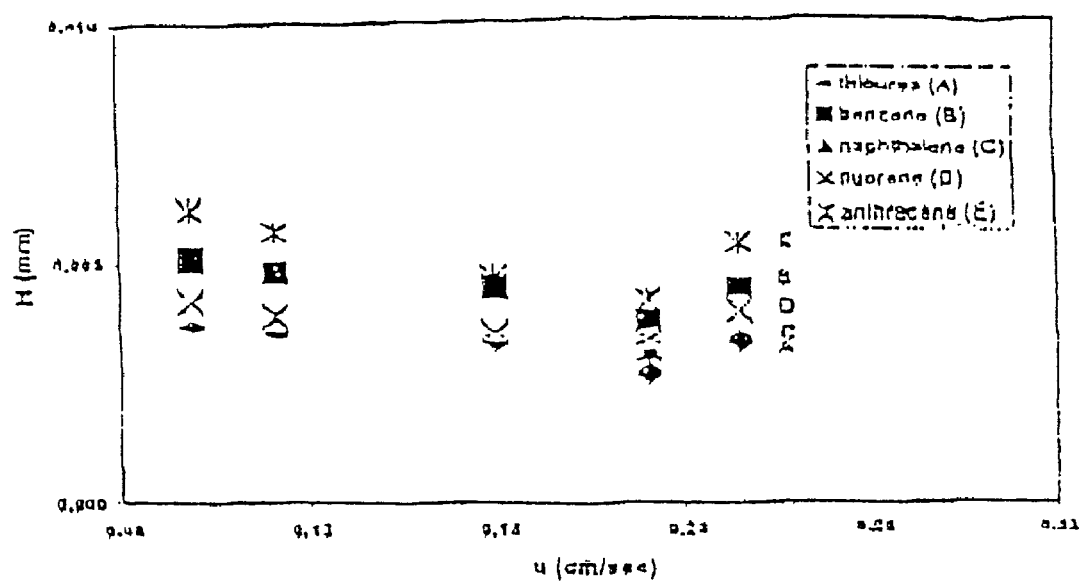
FIG. 6 is a plate height vs. mobile-phase velocity plots obtained on a sol-gel ODS coated OT-CEC column. Experimental conditions: capillary column, 25 $\mu$m i.d.×64 cm (inlet to detector); mobile phase 70:30 v/v ACN/Tris-HCl (5 mM, pH 2.34); injection 100 mbar 0.04 minutes; run −10 to −30 kV wherein the test solutes are: (A) thiourea, 4.76×10$^{-3}$M, (B) benzene, 53.9×10$^{-3}$M, (C) napthelene, 2.71×10$^{-6}$M, (D) fluorine, 1.54×10$^{-6}$M, (E) anthracene, 9.69×10$^{-7}$M.

Further characterization of this PheDMS-deactivated column is carried out by studying the dependence of plate height on mobile-phase inner velocity. For this, a series of varying applied voltages is used, keeping all other separation variables (e.g. injection conditions and mobile-phase composition) constant. The plate height versus mobile-phase linear velocity plot is depicted in FIG. 6. A careful analysis of this plot leads to several conclusions. For all test compounds, plate heights markedly decrease as the flow rates increase from 0.10 to 0.22 cm/s, followed by a slight rise occurring at higher velocities. This reveals that the optimum flow rate for these OT-CEC capillaries occurs at 0.22 cm/s, corresponding to an applied voltage of −25 kV (i.e. a field strength of ~373 V/cm). In OT-CEC, as in OT-LC, the analytes travel a significant radial distance through the mobile phase to interact with the stationary phase. For this reason, slower mobile-phase mass transfer that is typical of larger analytes adversely affect the separation efficiency at high mobile-phase velocities. Indeed, fluoranthene and pyrene show a slight increase in plate heights with an increase in mobile-phase velocity beyond.

Figure 7:
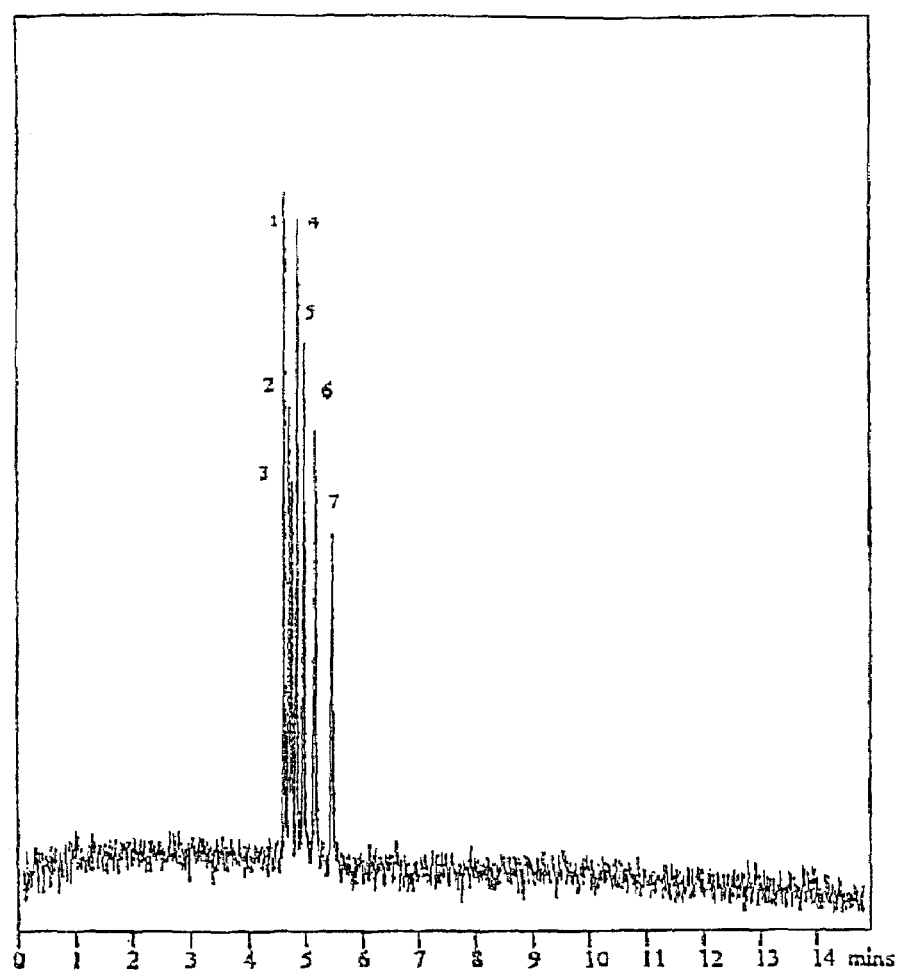
FIG. 7 is an OT-CEC separation of a test mixture of aromatic aldehydes and ketones using a PheDMS-deactivated sol-gel $C_{18}$ coated column. Separation conditions: capillary column, 25 $\mu$m i.d.×64 cm (inlet to detector); mobile phase 60:40 v/v ACN/Tris-HCl (5 mM, pH 2.34)

The OT-CEC separation of a probe mixture of aldehydes and ketones obtained on a PheDMS-deactivated ODS coated sol-gel column is illustrated in FIG. 7. Unlike the PAHs, these solutes are more polar (i.e., less hydrophobic). Successful separation of this test mixture provides substantial evidence in favor of the viability of 25 μm-i.d. sol-gel coated ODS columns for OT-CEC.

For this separation, the highest column efficiency is 404,000 theoretical plates/m for thiourea using a mobile phase containing 60% acetonitrile and 40% Tris-HCl (Table 3).

As for FIG. 8, it illustrates an OT-CEC separation of a test mixture of benzene derivatives on a PheDMS-deactivated sol-gel ODS column. In this analysis, the obtained separation efficiencies ranging between 204,000 theoretical plates/m (for butylbenzene) and 384,00 plates/m (for thiourea) are achieved on a 64 cm×25 μm i.d. PheDMS-deactivated sol-gel $C_{18}$ coated column. In all instances, the achieved efficiencies are comparable to those reported previously for sol-gel $C_8$ columns in OT-CEC by Guo and Colon (Guo et al.), who used open-tubular columns of much reduced internal diameter (e.g. 10–13 μm i.d.).

FIG. 9 represents the dependence of EOF on the pH of the buffer used in the mobile phase to run a PheDMS-deactivated sol-gel $C_{18}$ coated OT-CEC column. A set of three runs are conducted for each mobile-phase pH. A series of mobile phases consisting of 50:50 (v/v) ACN/5 mM Tris-HCl is prepared using Tris-HCl solutions with pH values in the range of 2.34 and 9.91. Thiourea is employed as the EOF marker, which is run under constant injection and applied voltage conditions throughout the entire range of mobile phase used. Additionally, thorough rinsing with each new mobile phase is essential to allow for adequate column equilibration prior to acquiring the results from each analysis. As is evident from the EOF versus mobile-phase pH plot, the EOF in the sol-gel ODS coated column switches direction as the mobile-phase pH changes from 2 to 10. A higher cathodic EOF occurs as the pH of the mobile phase is increased. This is a consequence of the increased negative charge on the column inner surface that results from the newly deprotonated silanol groups. This increased cathodic EOF competes with the anodic EOF associated with the positively charged surface coating. At a pH value of ~8.5, the column shows no net EOF. Thus, at this pH, the cathodic EOF generated by the surface negative charges (e.g., due to disassociated silanol groups) is counter-balanced by the anodic EOF generated by the positive charge of the quaternary amine moiety on the sol-gel $C_{18}$ coating. Therefore, a pH value of 8.5 approximately represents the isoelectric point of the sol-gel ODS coating.

Test mixtures of polycyclic aromatic hydrocarbons, benzene derivatives, and aromatic aldehydes and ketones have also been used to evaluate the CEC performances of both nondeactivated and deactivated open tubular sol-gel columns resulting in switchable electroosmotic flow. As a result, a pH value of ~8.5 has been found to correspond to the isoelectric point for the prepared sol-gel ODS coatings.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

REFERENCES

Bigham, S., et al. Anal. Chem. 74 (4) (2002), Web release date Jan. 9, 2002.
Brinker, C. et al. Sol-gel Science: The Physics and Chemistry of Sol-gel Processing, Academic Press: San Diego, Calif. (1990).
Bruin, G. et al. J. Chromatogr, 517, 557 (1990).
Chong, S. et al. Anal. Chem., 69, 3339 (1997).
Dittmann, M. et al. J. Microcolumn., 9, 399 (Sep. 1997).
Folestad, S. et al. Chromatogr, 391, 347 (1987).
Garner, T. W. et al. J. Chromatogr., 640,397 (1993).
Gohlin, K. et al. J. Chromatogr, 645, 41 (1993).
Gohlin, K. et al. J. Microcolumn, 3, 547 (1991).
Guo, Y., et al. Anal. Chem., 67, 2511 (1995).
Hayes, J. et al. J. Chromatogr., 695, 3 (1997).
Hayes, J. D. et al. Anal. Chem., 72, 4090 (2000).
Hibi, K. et al. J. Chromatogr, 175, 105 (1979).
Ishli, D. et al. J. Chromatogr, 185, 73 (1979).
Jorgenson, J. et al. J Pharm. Biomed Anal. 2, 191 (1984).
Jorgenson, J. W. et al. J. Chromatogr, 255, 35 (1983).
Malik, A. et al. In Applications of Solid-Phase Microextraction; Royal Society of Chemistry; London, U.K., Chapter 6, pp 73–91 (1999).
Pesek, J. et al. J. Chromatogr., 736, 255 (1996).
Pesek, J. et al. J. Chromatogr., 736, 313 (1996).
Pfeffer, W. D. et al. J. Chromatogr., 557, 125 (1991).

Rebscher, H., et al. Chromatographia., 38, 737 (1994).
Ruan, Y., et al. Chromatographia, 35, 597 (1993).
Sawada, H. et al. Electrophoresis., 20, 24 (1999).
Swart, R. et al. J. Chromatogr, 670, 25 (1994).
Tan, Z. et al. Anal. Chem., 69,581 (1993).
Took, P. et al. Chromatographia, 24, 617 (1987).
Tsuda, T. et al. J. Chromatogr, 214, 283 (1981).
Tsuda, T. et al. J. Chromatogr, 248, 241 (1982).
Van Berkel, et al. Chromatogr, 449, 345 (1990).
Van Berkel, et al. Chromatographia, 24, 739 (1987).
Wang, D., et al. Anal Chem., 69, 4563 (1997).
Yang, C. et al. Electrophoresis., 19, 2278 (1998).
Zhang, Y. et al. J. Liq. Chromatogr., 18, 3373 (1995).

TABLE 1

Names and Structures of All Sol-Gel Reagents Used in the Fabrication of Monolithic CEC Columns

| Reagent Function and Reagent Name | Reagent Structure |
|---|---|
| 1. Sol-gel copre-cursor-Tetra-methoxysilane (TMOS) | $H_3CO-Si(OCH_3)_2-OCH_3$ |
| 2. Sol-gel copre-cursor-N-Octa-decyldimethyl[3-(tri-methoxysilyl)propyl] ammonium chloride ($C_{18}$-TMS) | $CH_3-(CH_2)_{17}-{}^+N(CH_3)_2-(CH_2)_3-Si(OCH_3)_2-OCH_3 \cdot Cl^-$ |
| 3. Deactivation reagent-Phenyldimethylsilane (PheDMS) | $H_3C-Si(H)(CH_3)-C_6H_5$ |
| 4. Catalyst-Trifluoro-acetic acid (TFA) | $F_3C-C(=O)-OH$ |

TABLE 2

Separation Efficiency and Run-to-Run Repeatability Data for a Sol-Gel Open Tubular Capillary Electrochromatography Column Using Aromatic Hydrocarbons as Test Solutes[a]

| analyte | sepn effic. N (plates/column) | av $t_R$ (min) | s | RSD (%) (n = 9) |
|---|---|---|---|---|
| thiourea | 380 000 | 4.30 | 0.03 | 0.66 |
| benzene | 271 000 | 4.61 | 0.03 | 0.57 |
| naphthalene | 263 000 | 4.78 | 0.03 | 0.67 |
| fluorene | 383 000 | 4.91 | 0.03 | 0.55 |
| anthracene | 232 000 | 5.18 | 0.04 | 0.68 |
| fluoranthene | 195 000 | 5.48 | 0.03 | 0.55 |
| pyrene | 205 000 | 5.65 | 0.03 | 0.55 |

Figure 3:
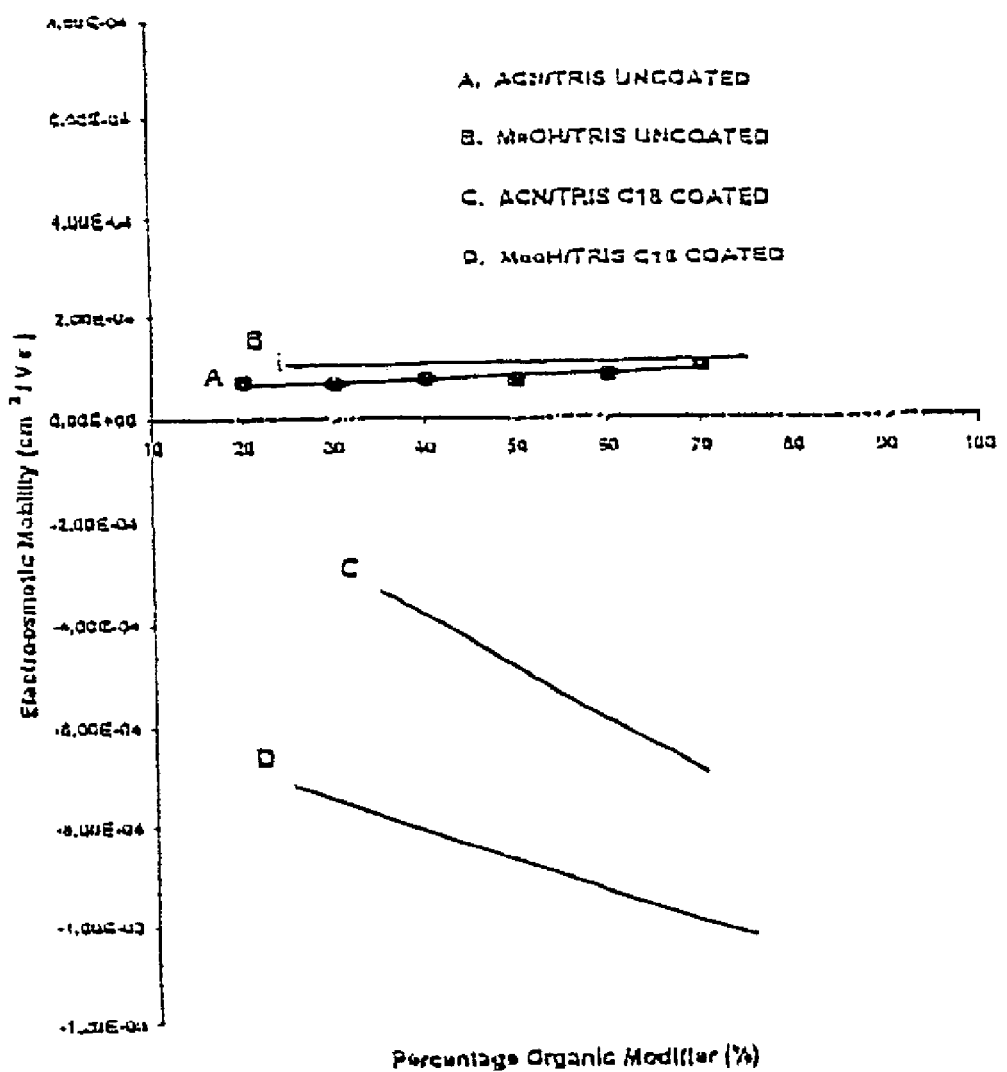
FIG. 3 is an evaluation of the effects of organic modifier on the EOF generated within both uncoated (A, B) and ODS coated (C, D) OT-CEC columns. Experimental Conditions: fused-silica capillary (70 cm×25 $\mu$m i.d.); injection for 0.04 minutes at 100 mbar; UV detection at 254 nm. (A) mobile phase 65:35 v/v ACN/Tris-HCl (pH 2.34), run +30 kV, −0.9 $\mu$A. (B) Mobile phase 65:35 v/v MeOH/Tris-HCl (pH 2.34); run +15 kV, −0.5 $\mu$A, (C) Mobile phase 65:35 v/v ACN/Tris-HCl (pH 2.34); run −30 kv, −0.7 $\mu$A. (D) Mobile phase 65:35 v/v MeOH/Tris-HCl (pH 2.34); run −15 kV, −0.5 $\mu$A.

[a]Experimental conditions: same as in FIG. 3

TABLE 3

Separation Efficiency and Run-to-Run Repeatability Data for a Sol-Gel Open Tubular Capillary Electrochromatography Column Using Carbonyl Compounds as Test solutes[b]

| analyte | sepn effic. N (plates/column) | av $t_R$ (min) | s | RSD (%) (n = 5) |
|---|---|---|---|---|
| thiourea | 404 000 | 3.92 | 0.03 | 0.66 |
| benzaldehyde | 232 000 | 4.01 | 0.03 | 0.75 |
| tolualdehyde | 231 000 | 4.06 | 0.03 | 0.70 |
| butyrophenone | 228 000 | 4.14 | 0.03 | 0.77 |
| valerophenone | 218 000 | 4.25 | 0.04 | 0.74 |
| hexanophenone | 202 000 | 4.40 | 0.04 | 0.79 |
| heptanophenone | 195 000 | 4.63 | 0.03 | 0.74 |

[b]Experimental conditions: same as in FIG. 4

Scheme 1.
Complete Hydrolysis of N-Octadecyldimethyl[3-(trihydroxysilyl)propyl] ammonium Chloride

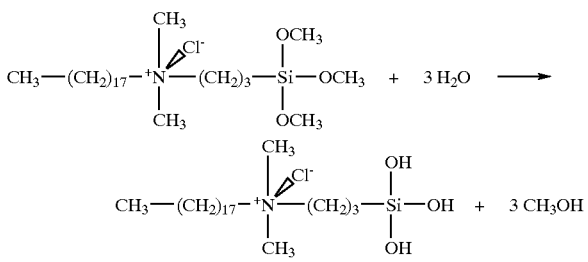

Scheme 2.
Condensation of Tetrahydroxysilane with N-Octadecyldimethy[3-(trihydroxysilyl)propyl]ammonium Chloride

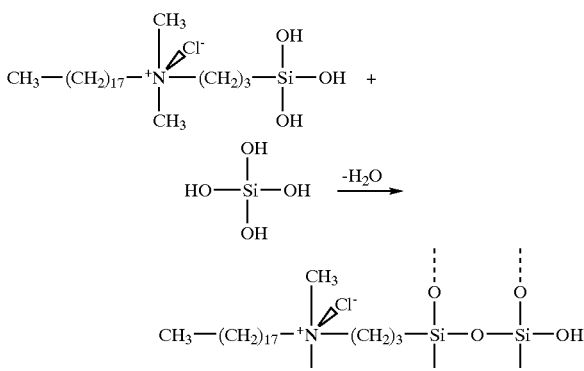

Scheme 3.
Bonding of the Sol-Gel ODS Coating with the Fused-Silica Surface[a]

A.

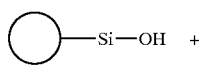

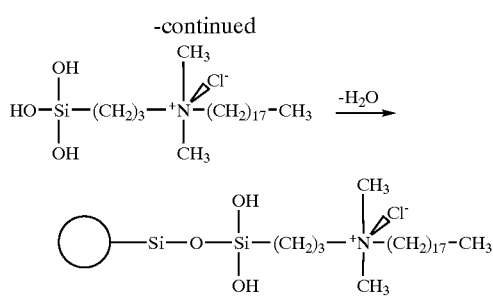

-continued

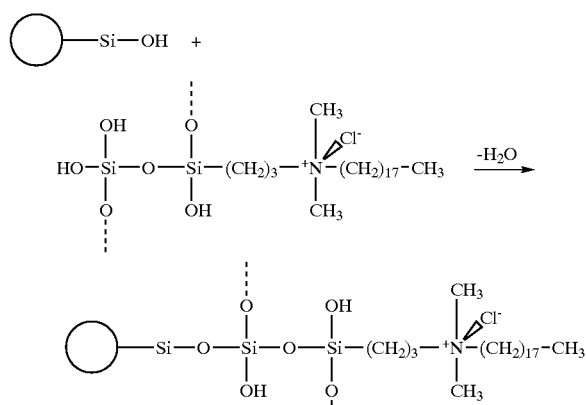

B.

a(A) Bonding of N-Octadecyldimethyl[3-(trihydroxysilyl)propyl] ammonium chloride with the fused-silica surface. (B) Bonding of the product of the condensation reaction of tetrahydroxysilane with N-octadecyldimethyl[3-(trihydroxysilyl)propyl]ammonium chloride with the fused-silica surface.

Scheme 4.
Deactivation of the Sol-Gel Mediated Fused-Silica Coated Surface with Phenyldimethylsilane (PheDMS)

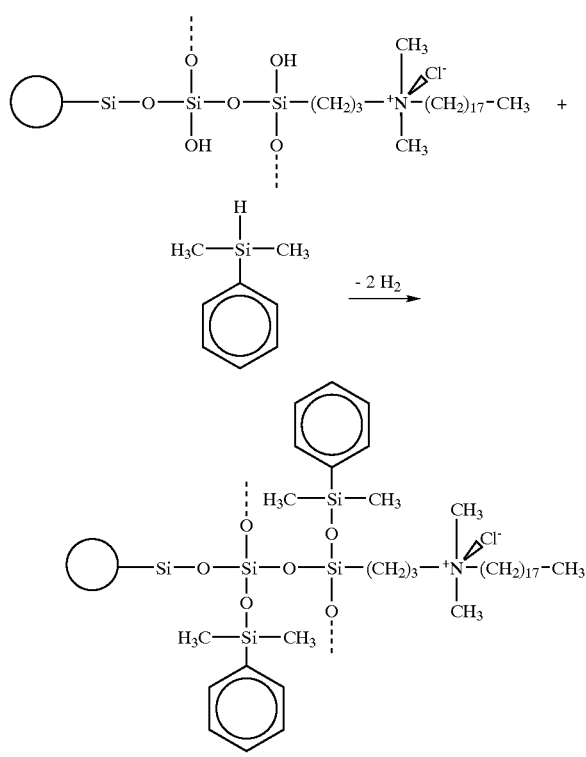

What is claimed is:

1. An open tubular capillary electrochromatography column for use in capillary electrochromatography comprising a tube, wherein said tube includes an inner surface having a charged, deactivated sol-gel bonded stationary coating thereon.

2. The open tubular capillary electrochromatography column according to claim 1, wherein said tube is defined as being made of materials selected from the group consisting of fused-silica, glass, titania, alumina, zirconia and polymeric hollow fibers with sol-gel active groups on the inner surface.

3. The open tubular capillary electrochromatography column according to claim 2, wherein said coating is defined as a sol-gel polymer including a positively charged moiety and chromatographic ligand.

4. The open tubular capillary electrochromatography column according to claim 3, wherein said positively charged moiety is a positively charged strong base.

5. The open tubular capillary electrochromatography column according to claim 3, wherein said positively charged moiety is selected from the group consisting of quaternary amine, nitrogen, and strong inclusion complexes of cations within cavities of moieties bonded to the capillary surface.

6. The open tubular capillary electrochromatography column according to claim 3, wherein said sol-gel polymer is formed from sol-gel precursors with reactive sol-gel reactive groups selected from the group consisting of alkoxy and hydroxyl groups.

7. The open tubular capillary electrochromatography column according to claim 3, wherein said sol-gel polymer includes a backbone having an inner metal selected from the group consisting of aluminum, titanium, silicon, zirconium, and vanadium.

8. The open tubular capillary electrochromatography column according to claim 3, wherein said chromatographic ligand is selected from the group consisting of $C_{18}$, $C_8$, cyanopropyl, $C_{12}$, $C_{30}$, crown ether, and cyclodextran.

9. The open tubular capillary electrochromatography column according to claim 3, wherein said sol-gel precursor is N-octadecyldimethyl[3-(trimethoxysilyl)propyl]ammonium chloride.

10. The open tubular capillary electrochromatography column according to claim 2, wherein said coating is defined as a sol-gel polymer including a negatively charged moiety and a chromatographic ligand.

11. The open tubular capillary electrochromatography column according to claim 10, wherein said negatively charged moiety is a negatively charged strong acid.

12. The open tubular capillary electrochromatography column according to claim 10, wherein said negatively charged moiety is selected from the group consisting of sulfonic acid groups and strong inclusion complexes of anions.

13. The open tubular capillary electrochromatography column according to claim 10, wherein said sol-gel precursors are selected from the group consisting of alkoxy groups and hydroxyl groups.

14. The open tubular capillary electrochromatography column according to claim 1, wherein said effective controlling of electroosmotic flow on the column comprises adjusting the pH of the mobile phase.

15. The open tubular capillary electrochromatography column according to claim 1, wherein said coating is defined as a sol-gel polymer including a positively charged moiety and chromatographic ligand; and wherein said effective controlling of electroosmotic flow on the column comprises adjusting the concentration of the positively charged moiety.

16. The open tubular capillary electrochromatography column according to claim 1, wherein said coating is defined as a sol-gel polymer including a negatively charged moiety and chromatographic ligand; and wherein said effective controlling of electroosmotic flow on the column comprises adjusting the concentration of the negatively charged moiety.

* * * * *

UNITED STATES PATENT AND TRADEMARK OFFICE
CERTIFICATE OF CORRECTION

PATENT NO. : 6,998,040 B2
APPLICATION NO. : 10/057080
DATED : February 14, 2006
INVENTOR(S) : Abdul Malik and James D. Hayes It is certified that error appears in the above-identified patent and that said Letters Patent is hereby corrected as shown below:

Column 7,
Line 14, "n-Octadecyidimethylmethoxysilane," should read -- n-Octadecyl dimethyl-methoxysilane, --.
Lines 14-15, "Methyl-n-Octadecyidiethoxysilane," should read -- Methyl-n-Octadecyl-diethoxysilane, --.
Line 18, "n-Ocyidi-isobutylmethoxysilane," should read -- n-Ocyldi-isobutyl-methoxysilane, --.
Line 19, "n-ctylmethyidimethoxysilane," should read -- n-ctylmethyldimethoxy silane, --.
Lines 28-29, "3-mercaptopropylmethyidimethoxysilane" should read -- 3-mercaptopropylmethyl dimethoxysilane --.
Lines 66-67, "N-tetradecyidimethyl" should read -- N-tetradecyldimethyl --.

Column 8,
Line 3, "N-trimethoxysilylpropyl-N,N,N,-" should read -- N-trimethoxysilylpropyl-N,N,N --.
Line 14, "n-Octadecyidimethylmethoxysilane," should read -- n-Octadecyldimethyl-methoxysilane, --.
Lines 28-29, "3-mercaptopropylmethyidimethoxysilane," should read -- 3-mercapto propylmethyldimethoxysilane, --.
Lines 31-33, "3-mercaptopropylcyanopropydimethoxysilane, 3 mercaptopropyl octa-decyidiethoxysilane," should read -- 3-mercaptopropylcyanopropyldimethoxysilane, 3- mercapto-propyloctadecyldiethoxysilane, --.
Line 52, "invention has a pi value" should read -- invention has a pI value --.

Column 15,
Line 48, "40% Tris-HCl" should read -- 40% tmM Tris-HC1 --.

Column 17,
Line 7, "Took, P. et al." should read -- Tock, P. et al. --.

Column 18,
Line 40, "N-Octadecyldimethy[3-" should read -- N-Octadecyldimethyl[3- --.

UNITED STATES PATENT AND TRADEMARK OFFICE
CERTIFICATE OF CORRECTION

PATENT NO.        : 6,998,040 B2
APPLICATION NO. : 10/057080
DATED             : February 14, 2006
INVENTOR(S)       : Abdul Malik and James D. Hayes It is certified that error appears in the above-identified patent and that said Letters Patent is hereby corrected as shown below:

Column 20,
Line 6, "thereon." should read -- thereon, that permits effective controlling of electroosmotic flow in the column. --.

Signed and Sealed this

Fourth Day of July, 2006

JON W. DUDAS
*Director of the United States Patent and Trademark Office*